US008877484B2

(12) United States Patent
Bau-Madsen et al.

(10) Patent No.: US 8,877,484 B2
(45) Date of Patent: Nov. 4, 2014

(54) MICROFLUIDIC DEVICE AND A MICROFLUIDIC SYSTEM AND A METHOD OF PERFORMING A TEST

(75) Inventors: Niels Kristian Bau-Madsen, Hellerup (DK); Jacques Jonsmann, Gørløse (DK); Søren Larsen, Copenhagen (DK)

(73) Assignee: Scandinavian Micro Biodevices APS, Farum (DK)

( * ) Notice: Subject to any disclaimer, the term of this patent is extended or adjusted under 35 U.S.C. 154(b) by 1094 days.

(21) Appl. No.: 12/522,756

(22) PCT Filed: Jan. 4, 2008

(86) PCT No.: PCT/DK2008/050001

§ 371 (c)(1), (2), (4) Date: Jul. 10, 2009

(87) PCT Pub. No.: WO2008/083687

PCT Pub. Date: Jul. 17, 2008

(65) Prior Publication Data

US 2009/0317793 A1 Dec. 24, 2009

Related U.S. Application Data

(60) Provisional application No. 60/879,524, filed on Jan. 10, 2007.

(30) Foreign Application Priority Data

Jan. 10, 2007 (DK) ................................ 2007 00035

(51) Int. Cl.
*C12M 1/00* (2006.01)
*B01L 3/00* (2006.01)

(52) U.S. Cl.
CPC ....... *B01L 3/50273* (2013.01); *B01L 3/502738* (2013.01); *B01L 3/502769* (2013.01); *B01L 2200/0621* (2013.01); *B01L 2300/0816* (2013.01); *B01L 2300/0864* (2013.01); *B01L 2400/0406* (2013.01); *B01L 2400/0688* (2013.01)
USPC ...................................................... 435/283.1

(58) Field of Classification Search
None
See application file for complete search history.

(56) References Cited

U.S. PATENT DOCUMENTS

| | | | |
|---|---|---|---|
| 4,233,029 | A | 11/1980 | Columbus |
| 4,618,476 | A | 10/1986 | Columbus |
| 4,756,884 | A | 7/1988 | Hillman et al. |
| 4,876,203 | A | 10/1989 | Guigan |
| 4,883,763 | A | 11/1989 | Holen et al. |
| 5,144,139 | A | 9/1992 | Hillman et al. |
| 5,230,866 | A | 7/1993 | Shartle et al. |
| 5,300,779 | A | 4/1994 | Hillman et al. |
| 5,443,890 | A | 8/1995 | Öhman et al. |
| 5,627,041 | A | 5/1997 | Shartle |
| 5,866,345 | A | 2/1999 | Wilding et al. |
| 6,084,660 | A | 7/2000 | Shartle |
| 6,090,251 | A | 7/2000 | Sundberg et al. |
| 6,451,264 | B1 | 9/2002 | Bhullar et al. |
| 6,488,827 | B1 | 12/2002 | Shartle |
| 6,575,188 | B2 | 6/2003 | Parunak |
| 6,591,852 | B1 | 7/2003 | McNeely et al. |
| 6,637,463 | B1 | 10/2003 | Lei et al. |
| 6,755,211 | B1 | 6/2004 | O'Connor et al. |
| 6,766,817 | B2 | 7/2004 | da Silva |
| 6,890,093 | B2 | 5/2005 | Karp et al. |
| 2001/0046453 | A1 * | 11/2001 | Weigl et al. .................. 422/102 |
| 2002/0003001 | A1 | 1/2002 | Weigl et al. |
| 2002/0048535 | A1 | 4/2002 | Weigl et al. |
| 2002/0119482 | A1 * | 8/2002 | Nelson et al. .................... 435/6 |
| 2002/0175151 | A1 | 11/2002 | Ohta et al. |
| 2003/0041652 | A1 | 3/2003 | Spaid et al. |
| 2003/0173630 | A1 | 9/2003 | Lin et al. |

(Continued)

FOREIGN PATENT DOCUMENTS

| | | | |
|---|---|---|---|
| DE | 103 34 341 | A1 | 3/2004 |
| DK | PA 2004 01913 | | 12/2004 |
| DK | PA 2005 00057 | | 1/2005 |
| DK | PA 2005 00732 | | 5/2005 |
| DK | PA 2005 01000 | | 7/2005 |
| EP | 0 831 679 | A1 | 3/1998 |
| EP | 0 974 840 | A2 | 1/2000 |
| EP | 1 221 617 | A2 | 7/2002 |
| EP | 1 224 976 | A1 | 7/2002 |
| EP | 1 304 167 | A1 | 4/2003 |

(Continued)

OTHER PUBLICATIONS

Official Action issued in U.S. Appl. No. 11/760,734, Dec. 10, 2009.

(Continued)

*Primary Examiner* — Ann Lam
(74) *Attorney, Agent, or Firm* — Buchanan Ingersoll & Rooney PC

(57) ABSTRACT

A microfluidic device comprising at least one test channel, which test channel comprises an upper test channel section with an upstream end and a sampling region at its upstream end and at least one reference channel, which reference channel comprises an upper reference channel section with an upstream end and a sampling region at its upstream end. The test channel and the reference channel comprise a merging region downstream to the upper test channel section and a common downstream channel section. The merging region and the common downstream channel section are arranged such that a reference liquid flowing from the upper reference channel section into the merging region will block a test liquid flow in the upper test channel section when the test liquid flow has not yet reached the merging section. The microfluid device may be used for detecting change of flow properties e.g. due to agglomeration, agglutination or viscosity change in a liquid preferably selected from water, urine, blood, or blood plasma.

35 Claims, 5 Drawing Sheets

(56) References Cited

U.S. PATENT DOCUMENTS

| | | | | |
|---|---|---|---|---|
| 2003/0178075 | A1 | 9/2003 | Moon et al. | |
| 2003/0185713 | A1 | 10/2003 | Leonard et al. | |
| 2003/0196714 | A1 | 10/2003 | Gilbert et al. | |
| 2004/0020399 | A1 | 2/2004 | Thiesen et al. | |
| 2004/0028566 | A1 | 2/2004 | Ko et al. | |
| 2004/0043506 | A1 | 3/2004 | Haussecker et al. | |
| 2004/0067166 | A1 | 4/2004 | Karinka et al. | |
| 2004/0191703 | A1 | 9/2004 | Soper et al. | |
| 2004/0202579 | A1 | 10/2004 | Larsson et al. | |
| 2004/0206399 | A1 | 10/2004 | Heller et al. | |
| 2004/0206408 | A1 | 10/2004 | Peters et al. | |
| 2004/0265172 | A1 | 12/2004 | Pugia et al. | |
| 2005/0000569 | A1 | 1/2005 | Bousse et al. | |
| 2005/0026346 | A1 | 2/2005 | Blankenstein et al. | |
| 2005/0087122 | A1* | 4/2005 | Ismagliov et al. | 117/2 |
| 2006/0018790 | A1 | 1/2006 | Naka et al. | |
| 2006/0048885 | A1 | 3/2006 | Constantin et al. | |
| 2006/0194342 | A1 | 8/2006 | Bond et al. | |
| 2006/0286000 | A1 | 12/2006 | Sundberg et al. | |
| 2007/0286774 | A1 | 12/2007 | Barholm-Hansen et al. | |
| 2008/0226502 | A1 | 9/2008 | Jonsmann et al. | |

FOREIGN PATENT DOCUMENTS

| | | | |
|---|---|---|---|
| FR | 2 846 906 | A1 | 5/2004 |
| GB | 2 341 924 | A | 3/2000 |
| WO | WO 99/58245 | A1 | 11/1999 |
| WO | WO 00/44207 | A1 | 7/2000 |
| WO | WO 00/56808 | A2 | 9/2000 |
| WO | WO 00/73090 | A1 | 12/2000 |
| WO | WO 2004/067444 | A1 | 8/2004 |
| WO | WO 2005/052594 | A1 | 6/2005 |
| WO | WO 2006/046054 | A1 | 5/2006 |
| WO | WO 2006/061025 | A2 | 6/2006 |
| WO | WO 2006/061026 | A2 | 6/2006 |
| WO | WO 2006/074665 | A2 | 7/2006 |

OTHER PUBLICATIONS

U.S. Appl. No. 11/813,835, Overby, et al.

Overby, Bent, et al., U.S. Appl. No. 11/813,835, entitled "Microfluidic Devices and Production Methods Therefor," filed Jul. 12, 2007.

International Search Report (PCT/ISA/210) mailed in PCT/DK2008/050001 May 29, 2008; EPO, Rijswijk, NL.

Letter from E. Silva, Ph.D., Dec. 13, 2007.

International Search Report mailed in PCT/DK2006/050002, Apr. 19, 2007, EPO, Rijswijk, NL.

Rossier, et al., "Topography, Crystallinity and Wettability of Photoabated PET Surfaces," *Langmuir*, 1999, pp. 5173-5178, vol. 15, No. 15, American Chemical Society, NY, NY, USA.

Michaeli, W., et al., "Broad range variation in surface tension by plasma-polymerized coatings on polymethyl methacrylate," *Surface and Coatings Technology*, 1993, pp. 338-341, vol. 59, Elsevier Sequoia, Lausanne, CH.

International Search Report and Written Opinion mailed in PCT/DK2006/050026, Apr. 5, 2007, EPO, Rijswijk, NL.

* cited by examiner

MICROFLUIDIC DEVICE AND A MICROFLUIDIC SYSTEM AND A METHOD OF PERFORMING A TEST

TECHNICAL FIELD

The invention relates to a microfluidic device for use in test of a liquid such as an agglutination test, and a coagulation test.

BACKGROUND ART

Microfluidic devices are widely used for performing tests of different types. The tests are generally performed on liquid samples which are applied to channels of microfluidic devices. In some tests the liquid sample is subjected to a reagent and dependant on change of a property and/or degree of change of a property of the liquid certain information about the liquid e.g. its composition, presence and/or amount of a certain component also referred to as an analyte can be concluded.

WO 2006/046054 and US2006/0194342 discloses a microfluidic device for an agglutination test. The device comprises a capillary pathway which incorporates a reagent system capable of causing agglutination with an analyte to be detected in a sample. The device may have two capillary pathways, one for the sample and one for a reference fluid. If the analyte is present in the sample an agglutination will occur and the liquid viscosity will increase which causes the liquid to flow slower than a reference sample which is not reacted with the reagent system. In certain circumstances the sample flow may almost stop. However in practice the agglutinated sample will never stop completely, and consequently the test system is highly inaccurate and the device has to be examined within a rather narrow time frame.

SUMMARY OF INVENTION

The object of the present invention is to provide a microfluidic device which is relatively simple and reliable to use in a test for examining if and/or to which degree a sample changes at least one property after being contacted with at least one reagent, such as an agglutination test and a coagulation test.

A further object of the invention is to provide a microfluidic system which is relatively simple and reliable to use in a test for examining if and/or to which degree a sample changes at least one property after being contacted with at least one reagent, such as an agglutination test and a coagulation test.

A further object is to provide a method for performing a test which is relatively simple to apply.

These and other objectives are fulfilled with the invention and/or its embodiments as they are defined in the claims and disclosed in the following.

The objects of the invention have been achieved by one or more of the accompanying claims.

The microfluidic device of the invention comprises at least one test channel comprising an upper test channel section with an upstream end and a sampling region at its upstream end and at least one reference channel comprising an upper reference channel section with an upstream end and a sampling region at its upstream end.

It is generally preferred that the an upper test channel section does not comprise any abrupt changes along it length from its sampling region til the merging region, so that a test liquid flow will continue to flow until the reference liquid flow has entered the merging region.

The test channel is the channel adapted to a sample which herein in general is designated a test liquid. The sampling region of the test channel is the region to which the test liquid can be applied, and from where it enters the upstream end of the test channel.

The reference channel is the channel adapted to a reference liquid. The sampling region of the reference channel is the region to which the reference liquid can be applied, and from where it enters the upstream end of the reference channel.

The test liquid is the liquid which is under examination, and the reference liquid is a liquid which is used for reference. As it will be clear from the description the test liquid and the reference liquid may be identical or they may be different from each other.

The test channel and the reference channel have a merging region and a common downstream channel section. The merging region is the region where the two channels, the test channel and the reference channel merges and the common downstream channel section is the section of the test channel and of the reference channel where they are unified.

The merging region and the common downstream channel section are arranged such that a reference liquid flowing from the upper reference channel section into the merging region will block a test liquid flow in the upper test channel section when said test liquid flow has not yet reached the merging section.

It is generally desired that when the reference channel has flown into the merging region it will block the upper test channel section so that no air can escape there from, which will result in termination of the test liquid flow in the upper test channel. In case the upper test channel section has additional openings for the escape of air, such openings should be blocked during the test.

In one embodiment the upper test channel, the merging region and the common downstream channel section are arranged such that a reference liquid flowing from the upper reference channel section into the merging region will block a test liquid flow in the upper test channel section at a point where it would not have been stopped without being blocked by the reference liquid in the merging region.

The device has thus provided a new tool for performing a test for examining if and/or to which degree a sample changes at least one property after being contacted with at least one reagent. The property may in principle be any property that changes the speed of flow of the test liquid in the test channel. The property may e.g. be a change in viscosity and/or a change in surface tension. The term property is used in singular, however it should be understood that the term 'property' also includes two or more properties.

In one embodiment the upper test channel section and the upper reference channel section have dimensions and/or surface tensions selected such that a liquid will flow from the sampling region of the reference channel to the merging region in a time T1 and from the sampling region of the test channel to the merging region in a time T2, wherein T1>T2, the liquid preferably being selected from the group of water, urine, blood, and blood plasma.

In use of a device of this embodiment the reference liquid is optimally a liquid which is akin to or even identical to the test liquid prior to reaction with reagent. This makes it therefore relatively simple to find a reference liquid which will work well.

The term dimension includes both the size of the channel, e.g. the cross-sectional area, as well as the shape. In principle the channels may have any shapes, the cross-sectional shape may e.g. be round, semi-round, square-shaped, rectangular or other e.g. as disclosed in WO06074665, WO06061026, WO0661025, DK PA 2005 00732.

The channels may in principle have any size, such as it is generally known within the art, and in dependence whether the device shall be adapted to work with or without the use of capillary forces.

The surface tension may e.g. be regulated using any method for example the method disclosed in any one of US 2004/0206399, US 2004/0265172 and DK PA 2005 00732.

The surface tension may be measured using a tensiometer, such as a SVT 20, Spinning drop video tensiometer marketed by DataPhysics Instruments GmbH. In this application the terms "surface tension" designate the macroscopic surface energy, i.e. it is directly proportional to the hydrophilic character of a surface measured by contact angle to water.

In one embodiment the device is arranged such that a liquid in the test channel and the reference channel will flow due to capillary forces and/or due to forces applied to the test channel and/or the reference channel.

'Forces applied' means herein forces applied from external source, such as a pressure element.

In one embodiment a pressure element is connected to one of the ends on at least one of the test channel and the reference channel. The pressure element is preferably adapted to apply a pushing pressure to the upstream end of at least one of the test channel and the reference channel and/or the pressure element is adapted to apply an pulling pressure to an end of the common downstream channel. In other words the pressure element is arranged to push and/or to pull the liquids into the respective channels and forward in the channel at least until the reference liquid has reached the common downstream channel.

The pressure element may for example be in the form of a chamber with at least one deformable wall section. The pressure can be generated by deforming the deformable wall section. If the pressure element is applied in the upstream end of the device the pressure will be generated while deforming the wall to decreasing the chamber size. This should preferably be performed under relatively controlled condition, preferably using a controlled instrument in order to make the test repeatable. If the pressure element is applied in the downstream channel of the device the pressure will be generated while a deformation of the wall is gradually returning to or approaching to original state prior to deformation. The deformation pressure may in this embodiment preferably be applied prior to applying the liquid or liquids in the sampling region(s).

The merging region and the common downstream channel section may preferably have dimensions and/or surface tensions selected such that a reference liquid flowing from the upper reference channel section into the merging region will block a test liquid flow in the upper test channel section when said test liquid flow has not yet reached the merging section.

In one embodiment the common downstream channel section in a distance from the merging region up to the difference in length between the upper test channel section and the upper reference channel section has a cross sectional area which is about or smaller than the cross sectional area of the upper reference channel section adjacent to the merging region, preferably the common downstream channel section adjacent to the merging region has a cross sectional area which is about or smaller than the cross sectional area of the upper reference channel section adjacent to the merging region. This structural feature in this embodiment may in particular be beneficial when the device is arranged to be used applying external forces to drive the liquid in the channel. However, it may also be very beneficial in devices adapted to using capillary forces to drive the liquid in the channel, because this structural feature may reduce the risk of capturing air bobbles from the upper test channel in the reference liquid in the merging region. Such capturing of bubbles may lead to uncertainties of the measuring result.

In one embodiment wherein the common downstream channel section comprises an opening for allowing gas within the channel to escape, preferably to the environment or to a pressure element connected to the common downstream channel section, the opening should preferably be arranged so that liquid flowing in the common downstream channel section does not flow out of the channel via said opening.

The opening may be of any size and shape such as it is generally known in the art. The gas in the channel is most often air, but it could as well be any other gas. The term 'escape' means that the gas can come out of the channel and the term 'environment' means outside of the device.

Arrangement for preventing the liquid to pass out via the opening may e.g. be a geometrical flow stop, a surface tension arranged flow stop and/or any other arrangements. Preferred method of providing a flow stop is described in DK PA 2005 01000.

The common downstream channel section may preferably be arranged as one single channel. However, on one embodiment the common downstream channel section comprises 2 or more lateral common downstream channel section segments, with equal or different shape and/or sizes The term 'common downstream channel section segments' that the common downstream channel section is separated into segments wherein liquid can flow from the merging region in a direction away from the upper test channel section and the upper reference region. The channel sections and segments may be arranged with any direction and configuration on the device—any distances in relating to the channel sections and segments is supposed to mean in relation to length through the respective channel segments and channel sections unless otherwise specified.

In one embodiment the lateral common downstream channel section segments are essentially parallel and in another embodiment the lateral common downstream channel section segments are non-parallel. In practice this feature relating to the configuration of the lateral common downstream channel section segments has only little or no influence of the function of the device.

The lateral common downstream channel section segments may each comprise an opening for allowing gas within the channel to escape, preferably to the environment or to at least one pressure element connected to the respective common downstream channel section segments. Also here the openings should preferably be arranged so that liquid flowing in the common downstream channel section does not flow out of the channel sections via said openings. Further information about this feature can be found above.

The upper test channel section and the upper reference channel section may be arranged with any angle to each other. In practice the upper test channel section and the upper reference channel section should preferably be separated at least 1 mm, such as at least 5 mm in order to provide a very clear and visibly detection of a flow front of a sample in the test channel.

In one embodiment the upper test channel section and the upper reference channel section has an angle to each other adjacent to the merging region between 15 and 90 degrees.

The angle should be measured as the lowest angle measured within a distance of up to 5 mm of each of the upper test channel section and the upper reference channel section to the merging region.

In one embodiment the test channel and the reference channel in the merging region forms a Y, or a T with the common downstream channel section. Any one of the 3 legs of the Y, or a T may be anyone of the channel sections.

In one embodiment the upper test channel section and the upper reference channel section has an angle to each other adjacent to the merging region of 25 degrees or more, such as 30 degrees or more.

In one embodiment the flow direction in the common downstream channel section adjacent to the merging region forms an angle to the flow direction in the upper test channel section adjacent to the merging region which is 25 degrees or more, such as 30 degrees or more In one embodiment the merging region comprises a dead end channel section, the dead end channel section preferably being adjacent to the upper test channel section and more preferably essentially opposite to the common downstream channel section.

A dead end channel is a channel section which does not allow air to escape and which is not adapted for puncturing. The dead end channel will consequently not be filled with liquid, but the liquid may enter a few millimeters into the channel due to capillary forces. By arranging a dead end channel in close relationship with the upper test channel section at the merging region a highly safe blocking of the upper test channel section when the reference liquid reaches the merging region.

In order to ensure an abrupt blocking of the upper test channel section once the reference liquid reaches the merging region, it is in one embodiment desired that the merging region, from the point of termination of respectively the upper test channel section and the upper reference channel section to a point where the a liquid common downstream channel section has a cross sectional area which is less than the cross sectional area of the upper reference channel section adjacent to the merging region (which is the point of termination), has a volume which is less than the total volume of the upper reference channel section, preferably 50% or less, such as 20% or less, of the total volume of the upper reference channel section.

The point of termination of respectively the upper test channel section and the upper reference channel section is respectively the upper test channel section immediately adjacent to the merging region and the upper reference channel section immediately adjacent to the merging region. This embodiment is particular relevant if the channels are not of capillary dimension, i.e. the device is arranged to apply forces to the test channel and/or the reference channel as explained above.

In one embodiment the upper test channel section immediately adjacent to the merging region has a cross-sectional area which is smaller than the cross-sectional area of the upper reference channel section longer away from the merging region.

It has been found that structuring the upper test channel section with a point of termination which is smaller than the point of termination for the upper reference channel section provide a very safe blocking of the upper test channel section once the reference liquid reaches the merging region. Furthermore, the risk of capturing air bubbles from the upper test channel section in the reference liquid in the merging region may be practically eliminated.

In one embodiment the upper test channel section immediately adjacent to the merging region has a cross-sectional area which is smaller than the cross-sectional area of the upper test channel section in a tapering distance to the merging region, the tapering distance preferably being between 1 and 20 mm.

The part of the upper test channel section from immediately adjacent to the merging region to the tapering distance being designated the tapering part. The tapering part may be tapering with one or more abrupt change of cross-sectional area or the change may be gradually along the length of the tapering part.

In one embodiment one or more of the channel sections of the device have shape and surface tension such that they the test and/or the reference liquid when applied in the respective channel sections is/are subjected to capillary forces. The capillarity for a given liquid of a channel section may vary along the length of it or it may be identical along the length of it. The capillarity may further be equal or different for a given liquid in the different channel sections. The capillarity for a given liquid of a channel section is the capillary forces which pull the liquid into and/or along a channel section to thereby wet the surface(s) of the channel section. The capillarity is dependant on the geometrical dimensions and the surface tension of the channel.

In one embodiment the common downstream channel section has a capillarity for water and/or blood measured at 20° C. which is equal to or lower than the capillarity of the upper reference channel section for water and/or blood measured at 20° C.

Thereby the reference liquid in case it water and/or blood is flowing as fast or faster while filling the upper test channel section than it is flowing into the common downstream channel section. Thereby risk of withdrawing and capturing air bobbles from the upper test channel section in the reference liquid in the merging region may be reduced.

In one embodiment the upper test channel section has a capillarity for water and/or blood measured at 20° C. which is equal to or lower than the capillarity of the upper reference channel section for water and/or blood measured at 20° C.

By arranging the capillarity of respectively the upper test channel section and the upper reference channel section the optimal ranges of lengths may accordingly be selected. Since it is generally desired that the reference liquid should reach the merging region prior to the test liquid, the reference liquid may preferably flow faster to the merging region than the test liquid—even if the test liquid is not reacted with a reagent.

In one embodiment the length of the test upper channel section measured from its upstream end to the merging region is longer than the length of the reference upper channel section measured from its upstream end to the merging region, preferably said upper test channel section is at least 10% longer, such as at least 50% longer than said upper reference channel section.

In one embodiment the upper test channel section has dimensions and surface tension so that a liquid having a surface tension of 40-80 mN/m, preferably a surface tension of 55-75 mN/m can be transferred in the upper test channel section by capillary forces.

In one embodiment the upper test channel section has dimensions and surface tension so that liquid such as blood and/or water e.g. at about 20° C. can be transferred from the sampling region to the merging region by capillary forces only, provided that the test channel is not blocked by liquid passing from the upper reference channel section into the common downstream channel section.

In one embodiment the upper reference channel section have dimensions and surface tension so that liquid such as blood and/or water e.g. at about 20° C. can be transferred from the sampling region to the merging region by capillary forces only.

In one embodiment the upper reference channel section has dimensions and surface tension so that a liquid having a surface tension of 40-80 mN/m, preferably a surface tension of 55-75 mN/m can be transferred in the upper reference channel section by capillary forces.

The surface tension within the respective channel sections may be modified using any method, e.g. by coating of a layer with the desired surface tension while for example simultaneously masking selected areas of the surface or removing surface layers using laser. A preferred method is disclosed in DK PA 2005 00732.

In one embodiment the upper test channel section and the upper reference channel section independent of each other, along the major part of their length have a smallest cross sectional dimension which is less than 1000 μm, such as in the range 1 μm-1000 μm, such as 25 μm-500 μm, such as 50 μm-250 μm.

In one embodiment the upper test channel section and the upper reference channel section along the major part of their length, such as along at least 60% of their length, such as along at least 70% of their length, such as along at least 80% of their length, such as along at least 90% of their length have a smallest cross sectional dimension which differs from each other with 100 μm or less, such as, 50 μm or less, such as 25 μm or less.

In one embodiment the upper test channel section and the upper reference channel section along the major part of their length, have essentially the same cross-sectional shape and size.

In order to visually inspect the channel section and in particular the upper test channel section or at least the part of the upper test channel section downstream to a reagent site the respective channels may be provided with a transparent wall section. In one embodiment at least a part of the wall section providing the upper test channel section being transparent, preferably the major part of the device is made from a transparent material.

The microfluidic device of the invention may in a preferred embodiment comprise at least one test channel, comprising an upper test channel section with an upstream end, a sampling region at its upstream end and a reagent, and at least one reference channel comprising an upper reference channel section with an upstream end and a sampling region at its upstream end, said test channel and said reference channel have a merging region and a common downstream channel section, and wherein the reagent is placed in the upper test channel section at a distance from said merging region.

The term 'reagent' is used to designate a reagent as such bud does also enclose a reagent system, i.e. a group of reagents which may be physically or chemically mixed or which may be used in discrete portions.

For simple handling it is often desired that the device have one single test channel. However the device may have 2 or more test channels, such as 3 or more, such as 4 or more, such as up to 10 test channels. For certain applications 2 or more test channels may be preferred, e.g. for blood type determination a device comprising 3 test channels may be desired—one for testing for antigens of type A, one for testing for antigens of type B, and one for testing for antigen Rh. The different tests may alternatively be performed on different devices. For performing parallel test a device comprising 2 identical test channels may e.g. be provided.

The 2 or more test channels may each comprise an upper test channel section with an upstream end, a sampling region at its upstream end and a reagent, said test channels and said at least one reference channel have a merging region and a common downstream channel section. The reagent may be placed in the upper test channel sections at a distance from said merging region. The reagent in the respective upper test channel sections may be different or equal in composition or in amount—e.g. different in concentration. The device may thus be used for determining an optimal amount of a reagent for obtaining a certain change of property of the test liquid.

The reagent in the respective upper test channel sections may be placed with a different distance to the sampling region for said respective upper test channel sections. The place of the reagent may be selected in accordance to the application, The length of the respective upper test channel sections of the 2 or more test channels may be equal or different from each other. The shape, the cross sectional area and the surface tension of the respective upper test channel sections of the 2 or more test channels may also be equal or different, depending on the desired application.

In one embodiment also the reference channel comprises a reagent. For certain application it is desired to compare property changes of a liquid while being subjected to different reagents or different amount of reagents. For certain application it is desired to subject the reference liquid to a reagent e.g. for reducing viscosity and/ore preventing agglutination and/or agglomeration.

In one embodiment the reference channel comprises a reagent placed in the upper reference channel section at a distance from said merging region. The reagent in said reference channel preferably being different in composition and/or amount from said reagent is said test channel.

The sampling region for the various upper test channel section(s) and/or upper reference channel section(s) may be in the form of separate sampling regions or two or more channel sections may share the same sampling region which means that said two or more channel sections have a common sampling region.

In one embodiment at least one upper test channel section and at least one upper reference channel have a common sampling region. By having a common sampling region for two or more channel sections, the liquid which is to be applied in the channels will be applied simultaneously and the flow in the respective channels can be initiated simultaneously. In order to obtain repeatable test result it is desired that the flow in the respective channels can be initiated simultaneously and this may be obtained by using this design.

In one embodiment at least one upper test channel section and at least one upper reference channel section have separate sampling regions.

The term 'that two or more channel sections have separate sampling regions' is supposed to mean that they do not have a common sampling region.

In one embodiment wherein the device comprises 2 or more upper test channel sections, at least two upper test channel sections have separate sampling regions. Thereby different test liquids can be used.

In one embodiment at least one upper test channel section has separate sampling region. The separate sampling region may e.g. comprise a reagent.

In one embodiment at least one upper test channel section comprises a reagent, said reagent being applied in a chamber of said upper test channel section. A chamber means in this contest a subsection of the channel which has a larger cross-sectional area that the average cross-sectional area of the channel section in question, such as a cross sectional area which is at least 25%, such as at least 50%, larger than the average cross sectional area of the channel section in question.

In one embodiment at least one upper test channel section comprises a reagent applied in a chamber having a cross sectional area which is at least 25%, such as at least 50% larger than the average cross sectional area of said upper test channel section.

In one embodiment at least one upper test channel section comprises two or more chamber with reagent, the reagent may be different or equal to each other.

In one embodiment at least one upper reference channel section comprises at least one chamber with reagent.

In one embodiment wherein at least one upper test channel section and/or at least one upper reference channel section comprises a reagent, at least one surface part of said upper channel section comprising a hydrophilic surface area and a hydrophobic surface area, wherein the hydrophobic surface area has a lower surface tension than the hydrophilic surface area, the hydrophobic surface area forms a pattern in the hydrophilic surface area, the pattern forms an island shaped segment, the island shaped segment preferably being formed by the hydrophobic pattern totally or partly shaped as one or more flow blocking lines, the central part of the island shaped segment, optionally having the surface layer of the higher surface tension, the reagent being applied onto the central part of the island shaped segment.

The island shaped segment may be as described DK PA 2005 00732 which with respect to the disclosure relating to the island shaped segment is hereby incorporated by reference.

In one embodiment at least one upper test channel section comprising at least one hindrance element for slowing down the velocity of the flow front of the test liquid in said test channel. The hindrance element may be in the form of a narrowing on the upper test channel section, in the form of elements protruding from the channel walls e.g. flanges essentially parallel to the channel direction, and or in the form of a secondary element e.g. a filter element inserted into the upper test channel section. The hindrance element should preferably be structured such that the test liquid without the analyte(s) which react with the reagent easily can pass through the hindrance element in the upper test channel section, whereas when the analyte(s) which react with the reagent is present in the test liquid and the test liquid has reacted with said reagent, the hindrance element provide an extra hindrance for the progress of the flow front through the upper test channel section. In embodiments where the reagent is applied in the upper test channel section, the hindrance element should preferably be arranged between the site of the reagent and the merging region.

In one embodiment of the microfluidic device for testing for an analyte in a test liquid wherein at least one upper test channel section comprises a reagent, this reagent is capable of binding to said analyte, preferably said reagent being selected to form a agglutination assay and or a coagulation assay.

In one embodiment the at least one upper test channel section comprises at least one reagent selected from an agglutination reagent and a coagulation reagent. Examples of reagents includes antibodies, antigens, enzymes, nucleic acids, such double stranded, partly single stranded and single stranded DNA, RNA, LNA and PNA.

In one embodiment of the microfluidic device for testing for an analyte in a test liquid the test liquid being blood or a blood fraction. The said assay may for example be a coagulation assay and the reference channel preferably comprises an anticoagulation reagent.

The device of the invention may be provided with an electronic sensor system for electronic read out. Such arrangement for determine whether or not a liquid is present at a certain point in simple to arrange by a skilled person.

The microfluidic device may for example be provided with an electrochemical sensor, comprising at least 2 electrodes applied in the upper test channel section. A first electrode may be applied at the point of the reagent or closer to the sampling region than the reagent and a second electrode may be applied between the reagent and the merging region, preferably at a distance to the reagent e.g. close to the merging region. These 2 electrodes—a first pair of electrodes—may be connected so that if both electrodes are wetted by the liquid in the test channel a reaction e.g. a light is obtained. A similar arrangement may be applied over the reference channel, e.g. with one of the electrodes placed after their merging region e.g. in the common downstream channel section—this secondary electrode pairs can be used to determine when the test is terminated. The first and the second pair of electrodes may share one electrodes placed in a common sampling region.

The invention also relates to a method of performing a test for an analyte in a test liquid. The method may preferably be carried out using a microfluidic device as described above.

The method of the invention comprises

- providing a microfluidic device for example as described above
- applying the test liquid in the sampling region of the upper test channel section,
- applying the reference liquid in the sampling region of said upper reference channel section,
- allowing the test liquid to flow with a flow front in the test channel,
- allowing the reference liquid to flow with a flow front in the reference channel,
- subjecting the liquid in said upper test channel section to a reagent for said analyte, and
- determining if the analyte is present in said test liquid by observing the position of the flow front of said test liquid in said upper test channel section when said reference liquid blocks the test liquid flow.

If the analyte is present in the test liquid the analyte will react with the reagent and at least one property of the test liquid will change. The property should preferably be either a change of surface tension of the test liquid and/or a change of viscosity. If the test liquid or part thereof solidifies, this will also be included under the meaning of the term ‘change of viscosity’.

The microfluidic device provided comprises at least one test channel comprising an upper test channel section with an upstream end and a sampling region at its upstream end and at least one reference channel comprising an upper reference channel section with an upstream end and a sampling region at its upstream end. The test channel and the reference channel have a merging region and a common downstream channel section, wherein the merging region and the common downstream channel section are arranged such that a reference liquid flowing from the upper reference channel section into the merging region will block a test liquid flow in the upper test channel section at a time where said test liquid flow has not yet reached the merging section.

The test liquid and the reference liquid may be different from each other but most often it is desired to use essentially identical liquids for the test liquid and the reference liquid.

The test liquid may be subjected to the reagent in different ways. In one embodiment the reagent is added to the test liquid to be applied in the sampling region of the upper test channel section prior to applying said test liquid in the sampling region of the upper test channel section.

The term 'the reagent is added' means that the reagent and the liquid in question is brought together, in other words the term also include adding the liquid in question to the reagent.

In one embodiment the reagent is added to the test liquid in the sampling region of the upper test channel section, and the reagent may preferably be present in the sampling region of the upper test channel section prior to application of the test liquid.

The reagent may for example be applied in the sampling region and be allowed to dry, such as it is well known in the art to prepare a microfluidic device with reagents.

In one embodiment the reagent is added to the test liquid in the upper test channel section. Also in this embodiment it may be desired that the reagent is applied in the upper test channel section prior to application of the test liquid.

As explained above the term reagent also includes reagent systems of e.g. two or more different reagents. The reagent may be applied in one two or more portions.

In one embodiment the test liquid is subjected to 2 or more reagents.

As explained above the reference liquid may also be subjected to a reagent. In one embodiment the method comprises subjecting the reference liquid to a reagent, and the reagent for subjecting to the reference liquid may preferably be different in amount or composition from the reagent subjected to the test liquid.

In one embodiment the reagent for subjecting to the reference liquid is added to the reference liquid in the upper reference channel section, and the reagent may e.g. be present in said upper reference channel section prior to application of the reference liquid.

In order to obtain results by the test which is as accurate as possible, it is in one embodiment desired that the reference liquid and the test liquid is initiating the flow in the respective channels essentially simultaneously. This simultaneously initiating of flow of the respective liquids can be provided for in different ways.

In one embodiment the method of performing a test for an analyte in a test liquid according to the invention, the common downstream channel section comprises an opening for allowing gas within the channel to escape. The method comprising
- blocking said opening,
- applying said test liquid in the sampling region of the upper test channel section,
- applying said reference liquid in the sampling region of said upper reference channel section,
- removing said blocking from said opening and allowing said test liquid and said reference liquid to flow into respectively said test channel and said reference channel.

In one embodiment the method of performing a test for an analyte in a test liquid according to the invention, the common downstream channel section comprises a puncture area, said method comprising
- applying said test liquid in the sampling region of the upper test channel section,
- applying said reference liquid in the sampling region of said upper reference channel section,
- generating a opening for allowing gas within the channel to escape by puncturing said puncture area, and allowing said test liquid and said reference liquid to flow into respectively said test channel and said reference channel.

A puncture area is a wall section of the common downstream channel section which is sufficiently soft and/or thin to be punctured manually by a needle. The puncture area should preferably be non-elastically or have a elasticity which is sufficiently low such that the opening will not close by itself.

As described the liquid flow may be adjusted or controlled by selecting the capillarity for the respective channel sections.

In one embodiment the common downstream channel section has a capillarity for the test liquid at 20° C. which is equal to or lower than the capillarity of the upper reference channel section for the test liquid at 20° C.

In one embodiment the upper test channel section has a capillarity for the test liquid at 20° C. which is equal to or lower than the capillarity of the reference channel section for the reference liquid at 20° C.

In one embodiment wherein the device comprises 2 or more test channels as described above, the method comprising applying a test liquid in the respective sampling regions of the test channels, the test liquid applied may be equal or different from each other, e.g. being different in concentration or composition.

Another method of initiating the flow of two or more liquids in the respective channels essentially simultaneously comprising providing two or more channel sections with a common sampling region as described above.

In one embodiment wherein at least one upper test channel section and at least one upper reference channel section have a common sampling region, and the method comprising applying the test and reference liquid which is identical, in said common sampling region.

In one embodiment where the device comprises 2 or more upper test channel sections and at least two upper test channel sections have a common sampling region, the method comprising applying the test liquid in the common sampling region.

The test may preferably be an agglutination test or a coagulation test. In embodiments where the test is an agglutination test or a coagulation test the microfluidic device may preferably comprise at least one hindrance element for slowing down the velocity of the flow front of the test liquid in the upper test channel section as described above.

The liquid may in principle be any kind of liquid preferably a biological fluid or a mixture of components comprising a biological fluid. Preferred test liquids is selected from the group consisting of blood, plasma, urine, saliva and mixtures thereof and mixture of any of the above mentioned fluids with a solvent such as water.

The reference liquid may be equal or different from the test liquid and may preferably be a biological fluid or a mixture of components comprising a biological fluid. Preferred reference liquid is selected from the group consisting of blood, plasma, urine, saliva and mixtures thereof and mixture of any of the above mentioned fluids with a solvent such as water.

The reagent may be any reagent capable of reacting with the analyte in question. The reagent may for example be agglutination reagent, preferably selected from the group consisting of antibodies, antigens, enzymes, nucleic acids, such double stranded, partly single stranded and single stranded DNA, RNA, LNA and PNA.

In one embodiment the reagent added to the test liquid being is a coagulation reagent such as Thromboplastin.

In one embodiment where a reagent is added to the reference liquid, said reagent added preferably being an anticoagulation reagent, such as citrate.

Further scope of applicability of the present invention will become apparent from the embodiments given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF DRAWINGS

Examples of embodiments of the invention will be described below with references to the drawings.

The figures are schematic and simplified for clarity, and they just show details which are essential to the understanding of the invention, while other details are left out. Throughout, the same reference numerals are used for identical or corresponding parts.

The outer shape of the microfluidic device is not shown in any of the figs. In principle the outer shape may be any shape e.g. rectangular for example as a slide.

Figure 1:
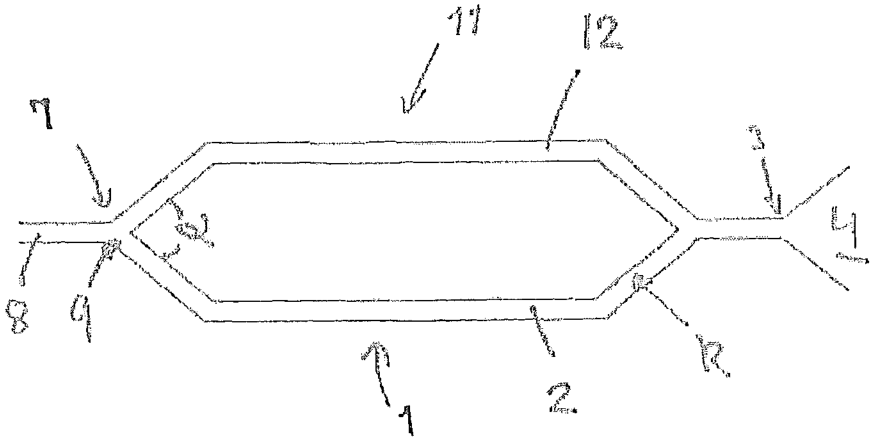
FIG. 1 is a schematic top view of a first microfluidic device of the invention.

FIG. 1 is a schematic top view of a first microfluidic device of the invention. The microfluidic device comprises a test channel 1 comprising an upper test channel section 2 with an upstream end 3 and a sampling region 4 at its upstream end 3 and at least one reference channel 11 comprising an upper reference channel 12 section with an upstream end 3 and a sampling region 4 at its upstream end 3. The upper test channel section 2 and the upper reference channel 12 section are arranged with an angle α to each other.

As it can be seen in this embodiment the test channel 1 and the reference channel 11 comprises a common sampling region 4 as well as a common upstream end 3.

The test channel 1 and the reference channel 11 have a merging region 7 and a common downstream channel section 8.

In the example shown in FIG. 1 the test channel 1 and the reference channel 11 have essentially same cross-sectional shape an essentially same length.

A not shown reagent may be incorporated in the upper test channel section 2 for example at a site marked with 'R'.

The common downstream channel section 8 should preferably comprise at least one opening for allowing gas within the channels to escape as the liquid flows into the channel.

In use the liquid—which constitutes both the test liquid and the reference liquid—is applied in the common sampling region 4, from where it due to capillary forces enters the test channel 1 and the reference channel 11 via the common upstream end 3. The test liquid flows along the upper test channel section 2 where it reaches the reagent at the site 'R'. Delaying element may be applied in the upper test channel section 2 as well as in the upper reference channel section 12. The delaying element may e.g. be inner surfaces of the channels which are relatively hydrophobic or other elements which can temporally delay or stop the flow.

As possibly analytes in the test liquid has been subjected to the reagent, the test liquid will change a property which will slow down or stop its flow in case the analyte is present. The reference liquid will continue flowing along the an upper reference channel 12 section until it reaches the merging region 7 from where it will flow further along the common downstream channel section 8. As the reference liquid enters the common downstream channel section 8, it will block the upper test channel section 2 at its point of termination 9. Thereby any flow in the upper test channel section 2 will stop immediately. The microfluidic device may thereafter be examined at any time by the user. The microfluidic device need not be examined immediately or at any specific time after termination of the test. Due to the blocking of the upper test channel section 2 the upper test channel section 2 is seal of and the microfluidic device may be examined at any time as desired by the user.

By performing a number of tests using liquids with known composition the microfluidic device may be calibrated. The upper test channel section may be provided with markings which can make the examination easier for the user.

Figure 2:
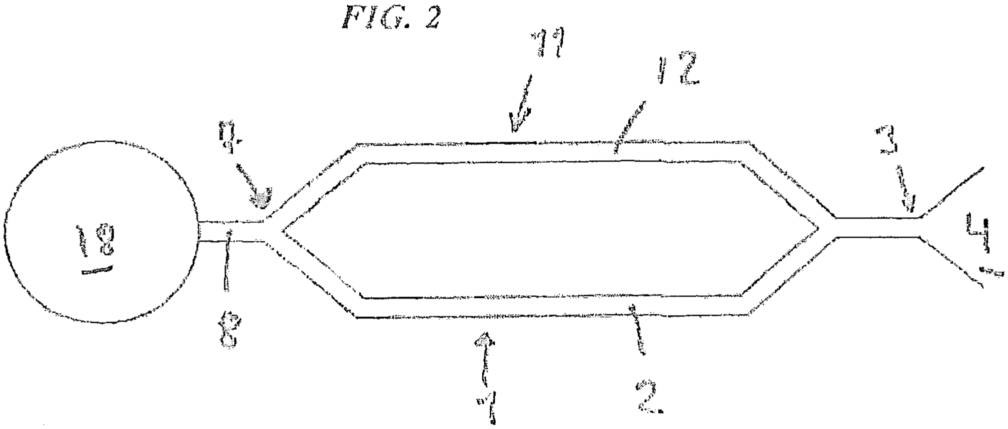
FIG. 2 is a schematic top view of a second microfluidic device of the invention.

FIG. 2 is a schematic top view of a second microfluidic device of the invention. The second microfluidic device differs from the first microfluidic device in that it comprises a pressure element 18 in the form of a chamber with at least one deformable wall section. The pressure can be generated by deforming the deformable wall section prior to application of the liquid in the common sampling region 4. The pressure element 18 is compressed, the liquid is applied in the common sampling region 4 where after the pressure applied to compress the pressure element 18 is removed and the force which will drive the liquid in the channels will be generated while the deformation of the wall is gradually returning to or approaching to original state prior to deformation. In this embodiment the various channel sections, 2, 12 and 8 need not apply capillary forces to the liquid.

Figure 3:
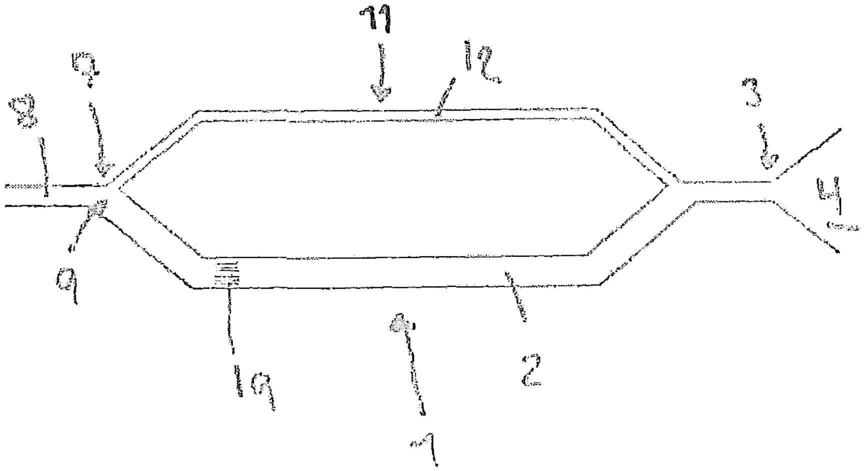
FIG. 3 is a schematic top view of a third microfluidic device of the invention.

FIG. 3 is a schematic top view of a third microfluidic device of the invention. The third microfluidic device differs from the first microfluidic device in that it comprises a hindrance element 19, and further more the dimension of the test channel 1 and the reference channel 11 differs from each other. The object of the hindrance element 19 is to slow down the velocity of the flow front of the test liquid in the upper test channel section 2. The hindrance element 19 is in the form of elements protruding from the channel walls and shaped as flanges essentially parallel to the channel direction. When a test liquid with an analyte has reacted with the reagent at site 'R' and the test thereby increases in viscosity, it may e.g. even react so as to generate solid elements in the test liquid. If the test liquid and thereby the flow front the test liquid even after the increase in viscosity continue flowing along the upper test channel section 2, the hindrance element 19 will slow down the velocity of the flow front of the test liquid. The hindrance element 19 is shaped such that is preferably does not provide any substantially hindrance of the flow of a test liquid without the analyte.

Figure 4:
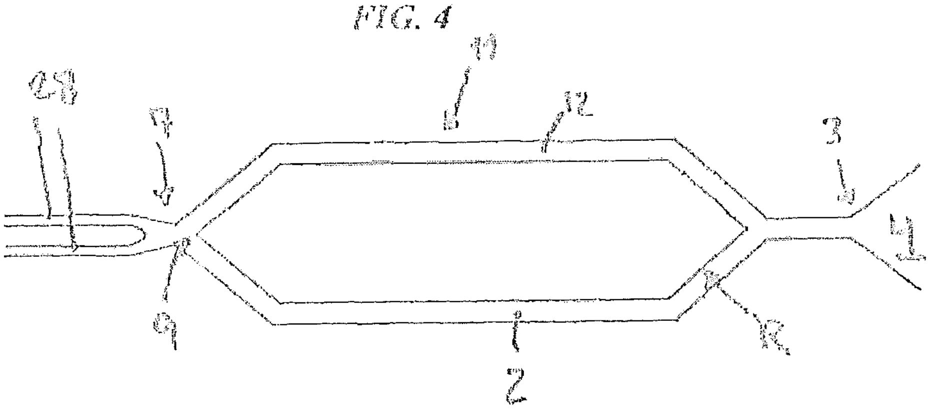
FIG. 4 is a schematic top view of a fourth microfluidic device of the invention.
Figure 5:
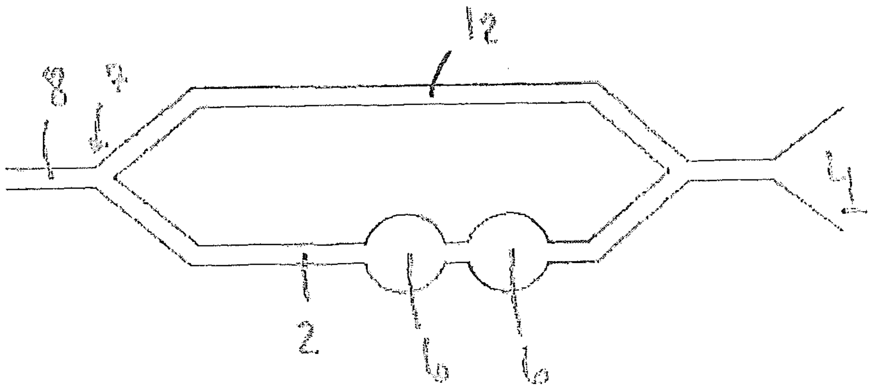
FIG. 5 is a schematic top view of a fifth microfluidic device of the invention.

FIG. 4 is a schematic top view of a fourth microfluidic device of the invention. The fourth microfluidic device differs from the first microfluidic device in that it comprises the common downstream channel section comprises 2 lateral common downstream channel section segments 28. As explained such lateral common downstream channel section segments 28 may have equal or different shape and/or sizes and they may be arranged with any direction and configuration on the device FIG. 5 is a schematic top view of a fifth microfluidic device of the invention. The fifth microfluidic device differs from the first microfluidic device in that the upper test channel section 2 comprises two chambers. One or both of the two chambers comprises a not shown reagent, e.g. applied in an island shaped segment as described above.

Figure 6:
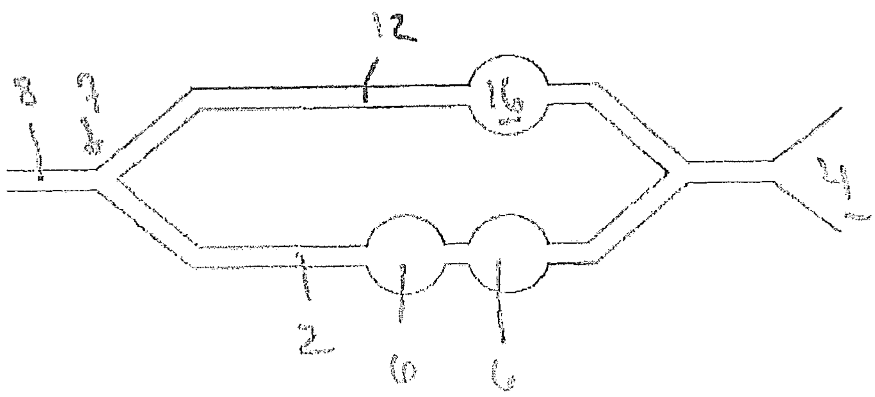
FIG. 6 is a schematic top view of a sixth microfluidic device of the invention.

FIG. 6 is a schematic top view of a sixth microfluidic device of the invention. The sixth microfluidic device differs from the fifth microfluidic device in that the upper reference channel section 12 additionally comprises a chamber 16 which further may comprise a not shown reagent.

Figure 7:
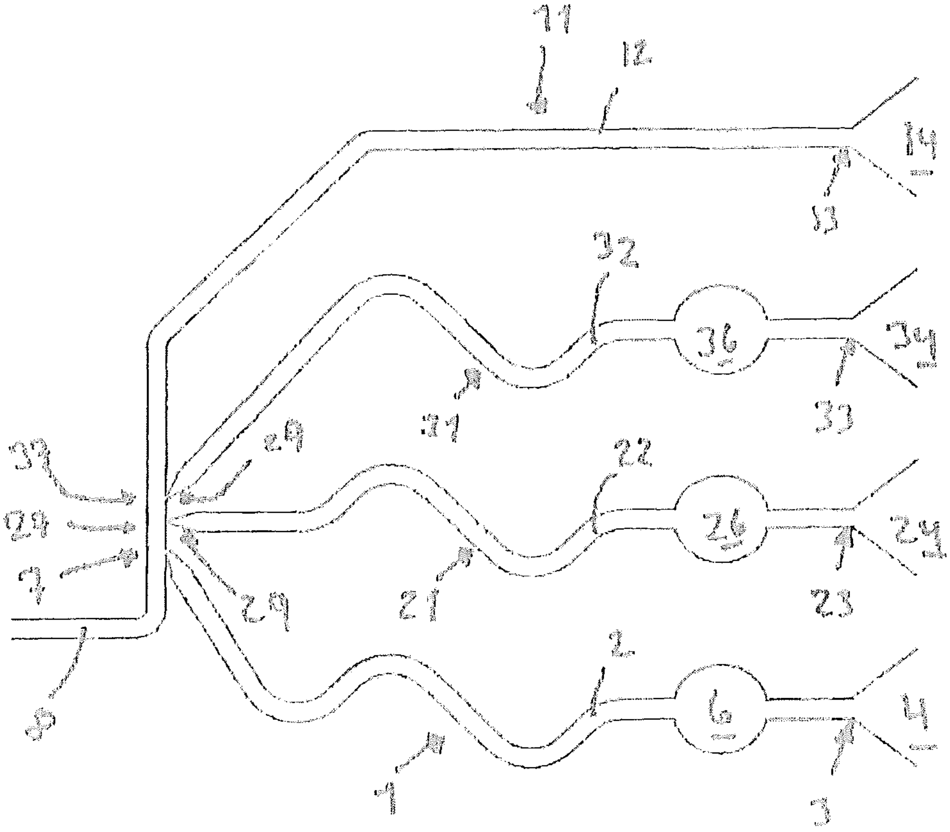
FIG. 7 is a schematic top view of a seventh microfluidic device of the invention.

FIG. 7 is a schematic top view of a seventh microfluidic device of the invention. The seventh microfluidic device differs from the first microfluidic device in that the microfluidic device comprises 3 test channels, 1, 21, 31, and furthermore each of the 3 test channels, 1, 21, 31 as well as the reference channel comprises separate sampling regions 4, 14, 24, 34.

The microfluidic device comprises a first test channel 1 comprising an upper test channel section 2 with an upstream end 3 and a sampling region 4 at its upstream end 3, a second test channel 21 comprising an upper test channel section 22 with an upstream end 23 and a sampling region 24 at its upstream end 23, a third test channel 31 comprising an upper test channel section 32 with an upstream end 33 and a sampling region 34 at its upstream end 33, and at least one reference channel 11 comprising an upper reference channel 12 section with an upstream end 3 and a sampling region 4 at its upstream end 3.

Each of the test channels 1, 21, 31 has a merging region 7, 27, 37 with the reference channel 11. All of the test channels 1, 21, 31 and the reference channel 11 have a common downstream channel section 8.

A not shown reagent may be incorporated in the upper test channel section of one or more of the upper test channel sections 2, 22, 32. As the test channels 1, 21, 31 and the reference channel 11 have separate sampling regions 4, 14, 24, 34, the reagent may as well be added to the liquid prior to application or alternatively any reagent may be placed in any one of the sampling regions 4, 14, 24, 34 prior to application of the respective liquids.

The upper test channel sections immediately adjacent to their respective merging regions 7, 27, 37 each has a cross-sectional area which is smaller than the cross-sectional area of the upper reference channel section longer away from the merging region. By applying such a tapering part of the respective upper test channel sections 2, 22, 32 the risk of capturing air bobbles from the upper test channel section in the reference liquid in the merging region may be reduced or even practically eliminated.

Figure 8:
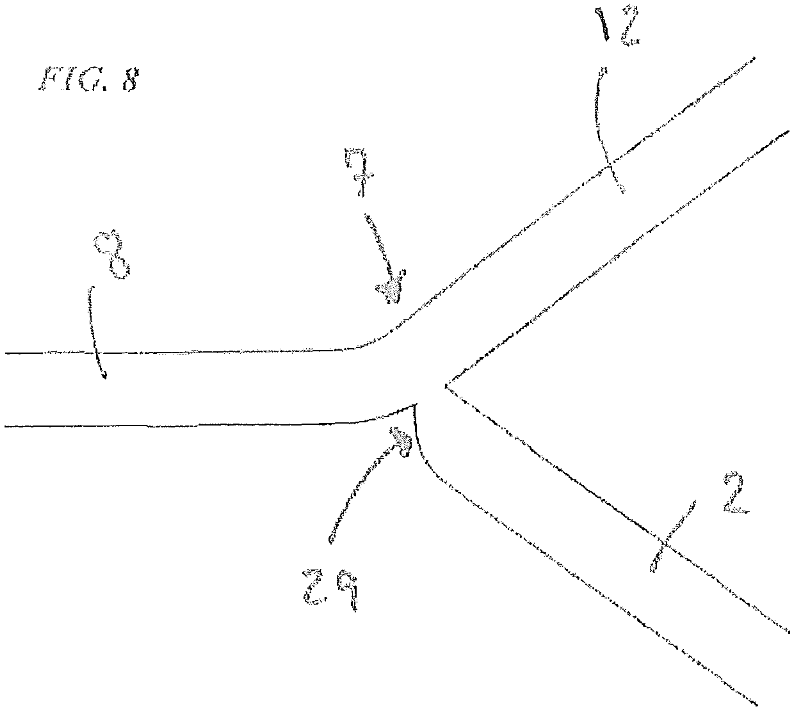
FIG. 8 is a schematic top view of an eighth microfluidic device of the invention.

FIG. 8 is a schematic top view of an eighth microfluidic device of the invention. FIG. 8 only shows a section of the device, namely the section comprising a part of the upper test channel sections 2, the upper reference channel 12, the common downstream channel section 8 and the merging region 7.

The upper test channel section 2 immediately adjacent to the merging region 7 has a cross-sectional area which is smaller than the cross-sectional area of the upper reference channel section at a distance from the merging region thereby forming a tapering part 29 where the tapering part 29 comprises a change of cross-sectional area which is gradually along the length of the tapering part.

Figure 9:
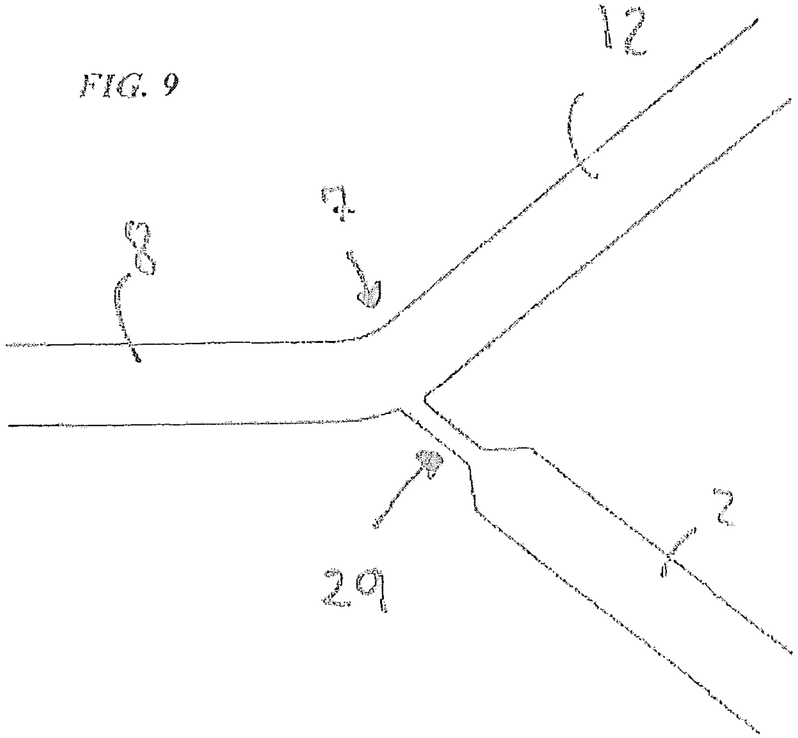
FIG. 9 is a schematic top view of a ninth microfluidic device of the invention.

FIG. 9 is a schematic top view of a ninth microfluidic device of the invention which only differs from the device in FIG. 8 in that the tapering part 29 comprises a change of cross-sectional area is in a relatively short distance from the merging region 7. In one not shown variation the tapering part is tapering with one, two or more abrupt change of cross-sectional area.

Figure 10:
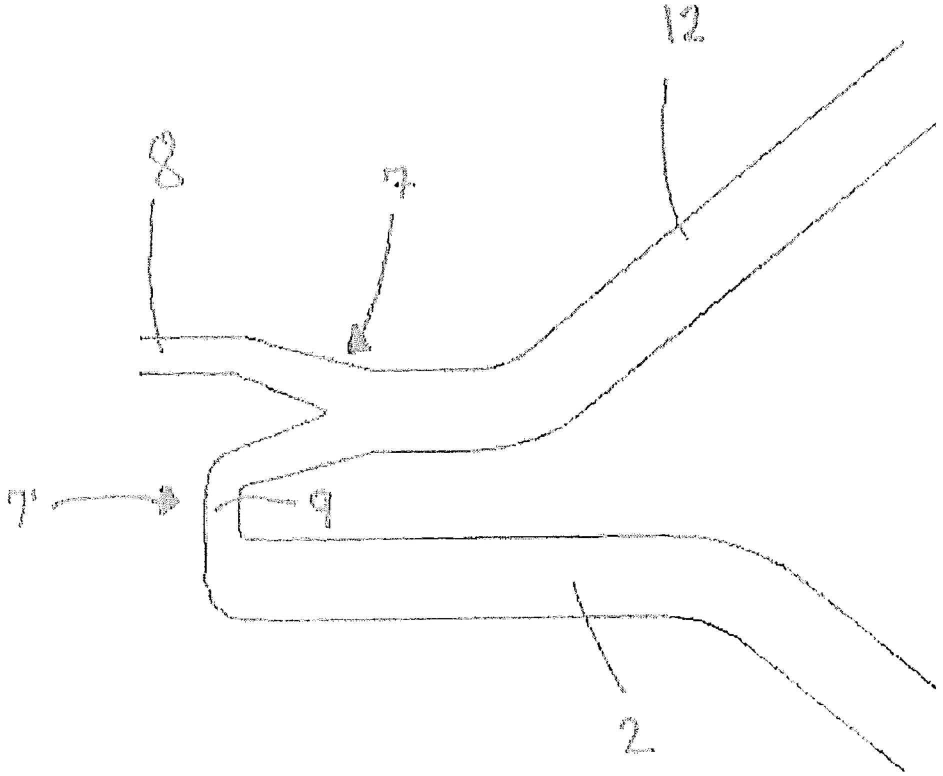
FIG. 10 is a schematic top view of a tenth microfluidic device of the invention.

FIG. 10 is a schematic top view of a tenth microfluidic device of the invention. The microfluidic device shown in FIG. 10 only shows a section of the device, namely the section comprising a part of the upper test channel sections 2, the upper reference channel 12, the common downstream channel section 8 and the merging region 7.

The upper test channel section 2 immediately adjacent to the merging region 7 has a bended part 7', and the cross-sectional area of the channel in at least a part 9 of said bended part is smaller than the cross-sectional area of the upper reference channel section at a distance from the merging region 7.

The bended part 7' is bended in a U bending. I variations the bending may have other shape and/or comprise several bends.

EXAMPLE

A coagulation test is performed using a microfluidic device as shown in FIG. 6. The liquid which is used both as test liquid and as reference liquid is undiluted blood from a cow.

A first coagulation reagent, Thromboplastin is applied in the chamber 6 of the upper test channel section 2 closest to the sampling region 4. A second coagulation reagent in the form of Thromboplastin plus calcium is applied in the other of the chambers 6 of the upper test channel section 2. An anticoagulation reagent (e.g. Citrat) is applied in the chamber 16 of the upper reference channel section 12.

The liquid is applied in the common sampling region 4 and it will immediately enter the upstream end 3 of the upper test channel section 2 and the upper reference channel section 12.

As the test liquid reaches the first chamber 6 it will react with the first reagent. The test liquid will flow into the second chamber 6 and react with the second reagent. As a result of the reaction the test liquid will at least partly coagulate if the tested blood comprises the amount of coagulation factors tested for and the test liquid flow will be very slow or almost stop.

The reference liquid will flow to the chamber 16 where it will react with the anticoagulant, and thereafter it will flow to the merging region 7 and into the common downstream channel section 8 while simultaneously blocking the upper test channel section 9 at its point of termination 9.

The invention claimed is:

1. A microfluidic device suitable for detecting a change in viscosity and/or surface tension of a sample, the microfluidic device comprising at least one test channel comprising an upper test channel section with an upstream end and a sampling region at its upstream end and at least one reference channel comprising an upper reference channel section with an upstream end and a sampling region at its upstream end, said sampling region of the test channel and said sampling region of the reference channel comprises a common sampling region, said test channel and said reference channel have a merging region downstream to said upper test channel section and a common downstream channel section and wherein the upper test channel section comprises at least one reagent selected from an agglutination reagent and a coagulation reagent and wherein the merging region and the common downstream channel section are arranged such that a reference liquid flowing from the upper reference channel section into the merging region will block a test liquid flow in the upper test channel section when said test liquid flow has not yet reached the merging section, wherein the upper test channel section and the upper reference channel section along the major part of their length, have a smallest cross sectional dimension which differs from each other with 100 μm or less.

2. The microfluidic device as claimed in claim 1 wherein the upper test channel section and the upper reference channel section have dimensions or surface tensions selected such that a liquid will flow from the sampling region of the reference channel to the merging region in a time T1 and from the sampling region of the test channel to the merging region in a time T2, wherein T1<T2.

3. The microfluidic device as claimed in claim 1 wherein the device is arranged such that a liquid in the test channel and the reference channel will flow due to capillary forces and/or due to forces applied to the test channel and/or the reference channel.

4. The microfluidic device as claimed in claim 1 wherein the merging region and the common downstream channel section have dimensions and/or surface tensions selected such that a reference liquid flowing from the upper reference channel section into the merging region will block a test liquid flow in the upper test channel section when said test liquid flow has not yet reached the merging section.

5. The microfluidic device as claimed in claim 1 wherein the common downstream channel section in a distance from the merging region up to the difference in length between the upper test channel section and the upper reference channel section has a cross sectional area which is about equal to or smaller than the cross sectional area of the upper reference channel section adjacent to the merging region.

6. The microfluidic device as claimed in claim 1 wherein the common downstream channel section comprises an opening for allowing gas within the channel to escape.

7. The microfluidic device as claimed in claim 1 wherein the common downstream channel section is in the form of one single channel or wherein the common downstream channel section comprises two or more lateral common downstream channel section segments, with equal or different shape and/or sizes.

8. The microfluidic device as claimed in claim 7 wherein said lateral common downstream channel section segments each comprises an opening for allowing gas within the channel to escape.

9. The microfluidic device as claimed in claim 1 wherein the upper test channel section and the upper reference channel section has an angle to each other adjacent to the merging region between 15 and 90 degrees.

10. A microfluidic device suitable for detecting a change in viscosity and/or surface tension of a sample, the microfluidic device comprising at least one test channel comprising an upper test channel section with an upstream end and a sampling region at its upstream end and at least one reference channel comprising an upper reference channel section with an upstream end and a sampling region at its upstream end, said sampling region of the test channel and said sampling region of the reference channel comprises a common sampling region, said test channel and said reference channel have a merging region downstream to said upper test channel section and a common downstream channel section and wherein the upper test channel section comprises at least one reagent selected from an agglutination reagent and a coagulation reagent and wherein the merging region and the common downstream channel section are arranged such that a reference liquid flowing from the upper reference channel section into the merging region will block a test liquid flow in the upper test channel section when said test liquid flow has not yet reached the merging section, wherein the upper test channel section immediately adjacent to the merging region has a cross-sectional area which is smaller than the cross-sectional area of the upper reference channel section immediately adjacent to the merging region.

11. A microfluidic device as claimed in claim 1 wherein the upper test channel section immediately adjacent to the merging region has a cross-sectional area which is smaller than the cross-sectional area of the upper test channel section in a tapering distance to the merging region.

12. The microfluidic device as claimed in claim 1 wherein the common downstream channel section and/or said upper test channel section has a capillarity for water and/or blood measured at 20° C. which is equal to or lower than the capillarity of the upper reference channel section for water and/or blood measured at 20 ° C.

13. The microfluidic device as claimed in claim 1 wherein said upper test channel section comprises a hindrance element for slowing down the velocity of the flow front of the test liquid in said test channel, said hindrance element preferably being in the form of elements protruding from the channel walls and/or in the form of a secondary element inserted into the upper test channel section.

14. The microfluidic device as claimed in claim 13 wherein said hindrance element being in the form of elements protruding from the channel walls and/or in the form of a secondary element inserted into the upper test channel section.

15. The microfluidic device as claimed in claim 1 wherein the upper test channel section has dimensions and surface tension so that a liquid having a surface tension of 40-80 mN/m can be transferred in the upper test channel section by capillary forces.

16. The microfluidic device as claimed in claim 1 wherein the upper reference channel section has dimensions and surface tension so that a liquid having a surface tension of 40-80 mN/m can be transferred in the upper reference channel section by capillary forces.

17. The microfluidic device as claimed in claim 1 wherein the upper test channel section and the upper reference channel section independent of each other, along the major part of their length have a smallest cross sectional dimension which is less than 1000 μm.

18. The microfluidic device as claimed in claim 1 wherein the upper test channel section and the upper reference channel section along the major part of their length, have essentially the same cross-sectional shape and size.

19. The microfluidic device as claimed in claim 1 wherein at least a part of the wall section providing the upper test channel section being transparent.

20. A microfluidic device comprising at least one test channel, comprising an upper test channel section with an upstream end, a sampling region at its upstream end, and at least one reference channel comprising an upper reference channel section with an upstream end and a sampling region at its upstream end, said sampling region of the test channel and said sampling region of the reference channel comprises a common sampling region, said test channel and said reference channel have a merging region and a common downstream channel section and wherein the upper test channel section comprises at least one reagent selected from an agglutination reagent and a coagulation reagent, said reagent being placed in the upper test channel section at a distance from said merging region; and wherein the merging region and the common downstream channel section are arranged such that a reference liquid flowing from the upper reference channel section into the merging region will block a test liquid flow in the upper test channel section when said test liquid flow has not yet reached the merging section; and wherein the upper test channel section and the upper reference channel section along the major part of their length, have a smallest cross sectional dimension which differs from each other with 100 μm or less.

21. The microfluidic device preferably as claimed in claim 20 wherein the length of the test upper channel section measured from its upstream end to the merging region is longer than the length of the reference upper channel section measured from its upstream end to the merging region.

22. The microfluidic device as claimed in claim 20 wherein said device comprises two or more test channels.

23. The microfluidic device as claimed in claim 22 wherein said two or more test channels each comprises an upper test channel section with an upstream end, a sampling region at its upstream end and a reagent, said test channels and said at least one reference channel have a merging region and a common downstream channel section, said reagent being placed in the upper test channel sections at a distance from said merging region.

24. The microfluidic device as claimed in claim 23 wherein said reagent in the respective upper test channel sections is different in composition or in amount.

25. The microfluidic device as claimed in claim 23 wherein said reagent in the respective upper test channel sections is equal in composition and in amount.

26. The microfluidic device as claimed in claim 23 wherein said reagent in the respective upper test channel sections is placed with a different distance to the sampling region for said respective upper test channel sections.

27. The microfluidic device as claimed in claim 22 wherein the length of said respective upper test channel sections is essentially equal to each other.

28. The microfluidic device as claimed in claim 20 wherein said at least one reference channel comprises a reagent said reagent being placed in the upper reference channel section at a distance from said merging region, said reagent in said reference channel preferably being different in composition and/or amount from said reagent is said test channel.

29. The microfluidic device as claimed in claim 20 wherein at least one upper test channel section comprises a reagent, said reagent being applied in a chamber of said upper test channel section, wherein said chamber is provided by a part of said upper test channel section having a cross sectional area which is at least 25 larger than the average cross sectional area of said upper test channel section.

30. The microfluidic device as claimed in claim 20 wherein at least one upper test channel section comprises a reagent, at least one surface part of said upper test channel section comprising a hydrophilic surface area and a hydrophobic surface area, wherein the hydrophobic surface area has a lower surface tension than the hydrophilic surface area, the hydrophobic surface area forms a pattern in the hydrophilic surface area, the pattern forms an island shaped segment, the reagent being applied onto the central part of the island shaped segment.

31. The microfluidic device for testing for an analyte in a test liquid as claimed in claim 20 wherein at least one upper test channel section comprises a reagent said reagent being capable of binding to said analyte.

32. The microfluidic device as claimed in claim 31 wherein at least one upper test channel section comprises a reagent said reagent being an agglutination reagent or a coagulation reagent.

33. The microfluidic device as claimed in claim 32 wherein said reagent being selected from antibodies, antigens, enzymes, nucleic acids, such double stranded, partly single stranded and single stranded DNA, RNA, LNA or PNA.

34. The microfluidic device as claimed in claim 20 wherein said device being provided with an electrochemical sensor, comprising at least two electrodes applied in said upper test channel section, a first electrode applied at the point of the reagent or closer to the sampling region than the reagent and a second electrode applied between the reagent and the merging region.

35. The microfluidic device as claimed in claim 1 wherein the upper test channel section and the upper reference channel section have dimensions and surface tensions selected such that a liquid will flow from the sampling region of the reference channel to the merging region in a time T1 and from the sampling region of the test channel to the merging region in a time T2, wherein T1<T2.

* * * * *